United States Patent
Harvey et al.

(10) Patent No.: US 7,231,920 B2
(45) Date of Patent: Jun. 19, 2007

(54) MEDICAMENT DISPENSER

(75) Inventors: Stephen James Harvey, Ware (GB); Paul Kenneth Rand, Ware (GB)

(73) Assignee: Glaxo Group Limited, Greenford (GB)

( * ) Notice: Subject to any disclaimer, the term of this patent is extended or adjusted under 35 U.S.C. 154(b) by 275 days.

(21) Appl. No.: 10/415,319

(22) PCT Filed: Oct. 19, 2001

(86) PCT No.: PCT/EP01/12106

§ 371 (c)(1), (2), (4) Date: Jul. 18, 2003

(87) PCT Pub. No.: WO02/36188

PCT Pub. Date: May 10, 2002

(65) Prior Publication Data

US 2004/0094152 A1 May 20, 2004

(30) Foreign Application Priority Data

Oct. 31, 2000 (GB) .................................. 0026647.8

(51) Int. Cl.
*A61M 16/00* (2006.01)
*H05B 3/00* (2006.01)

(52) U.S. Cl. ..................... 128/203.15; 128/202.22; 128/203.27; 604/59; 221/25

(58) Field of Classification Search ........... 128/203.21, 128/205.21, 200.24, 203.15, 203.12, 203.23, 128/203.14, 203.19, 203.24, 202.22, 203.27; 604/58–60; 116/282, 284, 289; 112/291; 606/61, 62, 67; 221/25

See application file for complete search history.

(56) References Cited

U.S. PATENT DOCUMENTS

| 5,590,645 | A | * | 1/1997 | Davies et al. .......... 128/203.15 |
| 5,622,166 | A | | 4/1997 | Eisele et al. |
| 5,829,435 | A | | 11/1998 | Cipolla et al. |
| 5,873,360 | A | | 2/1999 | Davies et al. |
| 5,896,855 | A | * | 4/1999 | Hobbs et al. .......... 128/203.15 |
| 5,921,237 | A | | 7/1999 | Eisele et al. |
| 5,971,951 | A | | 10/1999 | Ruskewicz |
| 6,116,238 | A | * | 9/2000 | Jackson et al. ........ 128/203.15 |
| 6,328,034 | B1 | * | 12/2001 | Eisele et al. ........... 128/203.15 |
| 2005/0017017 | A1 | * | 1/2005 | Crosby et al. ................. 221/25 |

FOREIGN PATENT DOCUMENTS

| EP | 0938907 | 9/1999 |
| GB | 2340758 | 3/2000 |
| WO | 9834664 | 8/1998 |
| WO | 9927987 | 6/1999 |
| WO | 9947099 | 9/1999 |
| WO | 0043287 | 7/2000 |
| WO | 0126720 | 4/2001 |

* cited by examiner

*Primary Examiner*—Justine R. Yu
*Assistant Examiner*—Shumaya Ali
(74) *Attorney, Agent, or Firm*—Robert J. Smith (57) ABSTRACT

According to the invention there is provided a medicament dispenser for use with a medicament carrier having a plurality of pockets for containing medicament wherein said pockets are spaced along the length of and defined between two peelable sheets secured to each other, said dispenser having an internal mechanism for accessing said medicament contained within said medicament carrier. The internal mechanism is operated by an electronic drive system.

30 Claims, 6 Drawing Sheets

MEDICAMENT DISPENSER

This application is filed pursuant to 35 USC 371 as a United States National Phase Application of International Patent Application Serial No. PCT/EP01/12106 filed 19 Oct. 2001, which claims priority from GB 0026647.8 filed on 31 Oct. 2001 in the United Kingdom, and PCT/EP00/12389 filed 9 Dec. 2000.

TECHNICAL FIELD

The present invention relates to a medicament dispenser for dispensing medicament. The invention particularly relates to a device for use in dispensing medicament in powder or tablet form.

BACKGROUND TO THE INVENTION

The use of inhalation devices in the administration of medicaments, for example in bronchodilation therapy is well known. Such devices generally comprise a body or housing within which a medicament carrier is located. Known inhalation devices include those in which the medicament carrier is a blister strip containing a number of discrete doses of powdered medicament. Such devices usually contain a mechanism of accessing these doses, usually comprising either piercing means or means to peel a lid sheet away from a base sheet. The powdered medicament can then be accessed and inhaled. Such a mechanism may also be used for dispensing medicament in tablet form wherein peeling away the lid sheet from the base sheet reveals a tablet for removal and subsequent consumption.

It is an object of the present invention to simplify the internal mechanism of a medicament dispenser for dispensing medicament in powder or solid form from a medicament carrier as described supra.

Yet another object of the present invention is to provide a device which is refillable by insertion of a replacement cassette containing a medicament carrier. The cassette may be replaced when the medicament carrier is empty. The device is therefore more 'environmentally friendly' as the majority of the device may be retained and is not disposable. It also allows the device to be fitted with additional features such as electronics which may not be cost effective on a completely disposable device.

It is a further object of the present invention that the cassette may be easily removed and that a new replacement cassette can be easily inserted. It is also desirable that the operation of the medicament dispenser be straightforward and non-complex and in particular that the number of separate steps involved in preparing the device for use be minimised. This is especially relevant where the device is designed for use in the delivery of medicament in emergency or rescue situations (e.g. asthma attacks) where simplicity and ease of use is paramount.

When not in use it is desirable from a hygiene standpoint that a mouthpiece, or other medicament exit channel, is provided with some kind of protective cover. The cover desirably acts both to prevent build-up of dirt and to prevent ingress of dirt into the body of the device through the mouthpiece or channel, which might then be subject to inhalation or consumption by a patient. It is also desirable that the cover is in some way attached or mounted to the device to minimise the risk that the cover is misplaced or lost. It is therefore a further object of the present invention for the body of the device to act as a mouthpiece or exit channel cover when the device is in storage and that the cassette is movable relative to the body to enable the mouthpiece or channel to be uncovered for use by the patient.

It is a further object of the invention to provide a medicament dispenser device suitable for use with a large number of discrete doses but which is of an acceptable size for use by patients.

SUMMARY OF THE INVENTION

Accordingly, in one aspect the invention provides a medicament dispenser for use with a medicament carrier having a plurality of pockets for containing medicament wherein said pockets are spaced along the length of and defined between two peelable sheets secured to each other, said dispenser having an internal mechanism for accessing said medicament contained within said medicament carrier, said mechanism comprising, a) an opening station for receiving a pocket of said medicament carrier;

b) peeling means positioned to engage a base sheet and a lid sheet of a pocket which has been received in said opening station for peeling apart such a base sheet and lid sheet, to open such a pocket, said peeling means including lid driving means for pulling apart a lid sheet and a base sheet of a pocket that has been received at said opening station;

c) an outlet, positioned to be in communication with an opened pocket through which a user can remove medicament from such an opened pocket; and d) indexing means for indexing in communication with said outlet, pockets of a medicament carrier in use with said medicament dispenser, wherein said lid driving means and/or said indexing means are operated by an electronic drive system.

The electronic drive system may also be used in conjunction with a mechanical drive system.

The drive means typically comprises a motor, preferably an electrically-powered motor. The motor may provide linear or rotary drive, but in general, rotary motors are most suitable. The motor may for example, comprise a DC electric motor, a piezoelectric (PZ) motor, an ultrasonic motor, a solenoid motor or a linear motor. Preferably, the electronic drive system comprises a DC motor, a PZ motor or an ultrasonic motor.

The use of ultrasonic motors is particularly preferred since they offer advantages over conventional motors in terms of weight, size, noise, cost and torque generated. Ultrasonic motors are well known in the art and are commercially available (e.g. BMSTU Technological Cooperation Centre Ltd, Moscow, Russia; Shinsei Corporation, Tokyo, Japan).

Ultrasonic motors do not use coils or magnets but comprise a piezo-electric ceramic stator which drives a coupled rotor. The stator generates ultrasonic vibrations which in turn causes rotation of the rotor. While regular DC motors are characterised by high speed and low torque, requiring reduction gearing to increase torque, ultrasonic motors attain low speed and high torque, thus eliminating the need for reduction gearing. Furthermore, these motors are lightweight and compact, lacking coils and magnets, and are noiseless as the ultrasonic frequencies used are not audible to the human ear.

Suitably, the dispenser further comprises actuating means for actuating said electronic drive system. Said actuating means may take the form of a switch, push-button, or lever.

Suitably, said indexing means comprises a rotatable index wheel having a recesses therein, said index wheel being engageable with a medicament carrier in use with said medicament dispenser such that said recesses each receive a respective pocket of the base sheet of a medicament carrier in use with said medicament dispenser.

Suitably, said rotatable index wheel additionally comprises a series of indentations located at its base and spaced in between the recesses.

Suitably, the indexing means additionally comprises an interlock coupling to couple actuation of the dispenser to the index wheel. The interlock coupling reversibly locks the index wheel in place. Preferably, said interlock coupling comprises a foot portion having a toe and a heel, and a tail section. Preferably, said interlock coupling is pivotally mountable to the dispenser at its foot portion. Preferably, said toe fits into one of the indentations on the rotatable index wheel. Preferably, the interlock coupling is sprung to bias it towards location of the toe in one of the indentations.

Alternatively, said indexing means comprises a gear and sprocket wherein teeth on the wheel fit into apertures or holes formed on one or both edges of the medicament carrier (e.g. blister strip). The mechanism therefore resembles that of photographic film being advanced through a camera.

Alternatively, said indexing means comprises an index ratchet which is moveable between a locked position whereby said ratchet engages a pocket on said medicament carrier and prevents further peeling thereof, and a release position allowing free movement of said medicament carrier. In this embodiment, actuation of said medicament dispenser actuates said lid driving means and releases said index ratchet from said medicament carrier to, allow peeling thereof.

Suitably, said lid driving means comprises a wheel on which the lid sheet is wound up, said wheel having a winding surface which decreases in diameter when tension in the lid sheet increases. Preferably, said wheel comprises a plurality of resiliently flexible arms each extending therefrom at an angle with respect to a radius. The leading end of the lid sheet is looped over one of said resiliently flexible arms to secure the lid sheet to the wheel initially.

In one aspect, the lid driving means comprise a mangle. The lid sheet passes through two rotating wheels which act as a mangle and is gripped at the point of contact with the wheels. The used portion of the lid sheet is collected in a chamber after it has passed through the mangle.

In another aspect, the lid driving means comprise a roller. Preferably said roller is composed of a polymeric rubber and is positioned next to a guide wall. Preferably said roller has a smooth surface. Alternatively said roller has a knurled surface. The roller grips the lid sheet as it passes from the point at which it is separated from the base sheet through the space between the roller and the guide wall and the used portion of the lid sheet is then collected in a chamber. The roller has the advantage over the mangle described above in that a greater degree of contact between the roller wheel and the lid sheet occurs—the lid sheet is squeezed through the roller and may pass around about ⅓ of the roller wheel. This provides a higher level of grip and pulling force than with a mangle. The force required to turn the roller is constant throughout the use of the device and does not vary according to how much of the lid sheet has been peeled away from the base sheet. This is in contrast to the wheel described above where the forces required to turn the wheel may vary due to the fact that the lid sheet is wound around the wheel. The lid sheet is not wound around the roller. The roller also has the advantage that the lid sheet does not have to be looped around or fixed to the roller before use of the device, therefore simplifying assembly of the device and reducing costs.

In a further aspect, the lid driving means comprise a lid spool. The lid spool comprises a toothed wheel with a central upward cylindrical projection on which the lid sheet may be wound when it has been separated from the base sheet. The lid spool may have a mechanical gearing mechanism which is driven on actuation of the dispenser; the lid sheet is pulled away from the base sheet and wound onto the lid spool, causing the rotatable indexing wheel to turn and index the base strip by one dose. An interlock coupling, as described supra, may be moved along the base of the rotatable indexing wheel until it fits into the next base recess. The positioning of the interlock coupling in this recess limits the movement of the lid spool to the distance between two pockets on the base sheet and therefore prevents the amount of lid sheet which is wound around the lid spool from increasing as the diameter of the lid spool is increased.

Suitably, said lid driving means comprises a wheel on which the lid sheet is wound up. Typically, said lid sheet wheel has an effective winding surface, the diameter of which increases after every use of the dispenser as the lid sheet winds around the wheel.

In order to ensure that the same dose is dispensed every time, that is, only one medicament pocket is opened for every actuation of the dispenser, the electronic control system may comprise means to limit the extent of movement of said lid driving means, in order to control the length of medicament carrier peeled by said peeling means. Hence, the medicament carrier is indexed by the same amount each time and a uniform, consistent dose is always dispensed.

The dispenser may further comprise compensating means positioned between said opening station and said lid sheet wheel for reducing the length of said lid sheet therebetween to compensate for any increase in the diameter of the effective winding surface of the lid sheet wheel during use of the dispenser.

Typically, the compensating means takes the form of a flexible member. The flexible member may take the form of a flexible elongate arm about which the lid sheet is fed. The arm may flex inwards as tension in the lid sheet increases, and thus shorten the length of lid sheet between the opening station and the lid driving means.

Suitably, the compensating means takes the form of a spring which reduces in length as tension increase in the lid sheet between the opening station and the lid driving means. Typically a piston head is mounted on one end of the spring about which the lid sheet is fed. The other end of the spring may be fixed. As tension in the lid sheet increases the piston is driven down onto the spring.

Suitably, the compensating means takes the form of a sprung-loaded tensioner.

Suitably, the flexible member is resilient so that on removal of tension from the lid sheet, the flexible member will return to its rest position. Thus, the internal mechanism can be reloaded with a new medicament carrier after the used carrier is removed.

Alternatively, or in addition, the dispenser may comprise a clutch means to adjust for any increase in the diameter of the effective winding surface of the lid driving means during use of the dispenser. In one aspect, the clutch means communicates with the indexing means and the lid driving means, and comprises a gearing surface defining plural gear engagement positions; and plural gear teeth for engaging said plural gear engagement positions, wherein the plural gear teeth are arranged such that at any one time only a single gear tooth engages a single gear engagement position.

It will be appreciated that, in use, the clutch means acts to compensate for the increase in diameter of said effective winding surface of the lid driving means. The clutch means allows for slippage when the tension in the lid sheet is greater than the force required to peel apart the lid sheet and the base sheet.

It will be appreciated that in total, the clutch means effectively defines a number of individual gear positions which is greater than the number of gear engagement positions. This is therefore advantageous over a traditional slipping clutch arrangement comprising intermeshing gear wheels, where the effective number of individual gear positions defined is either equal to, or no more than, the number of gear engagement positions defined by one of the gear wheels. The clutch means herein is also typically more compact than traditional slipping clutch arrangements e.g. because it enables smaller gearing surfaces to be employed.

In a preferred aspect, the gearing surface and plural gear teeth are arranged such that the number of individual gear positions defined is equal to the number of gear engagement positions multiplied by the number of gear teeth. In one example, if the gearing surface defines 60 gear engagement positions and there are 6 gear teeth, then up to 360 individual gear positions are definable (e.g. 1° resolution on a rotating gear system).

Suitably, the gearing surface defines from 20 to 100, preferably from 40 to 80 gear engagement positions. Suitably, the number of gear teeth is from 2 to 20, preferably from 3 to 10.

In one aspect, the gear engagement positions are equally spaced (e.g. equidistantly spaced) and the gear teeth are offset (e.g. non-equidistantly spaced) relative thereto. Such offset arrangement maximises the number of effective individual gear positions which are capable of definition. An example of this aspect, is a Vernier spring arrangement.

In another aspect, the gear engagement positions are also equally spaced (e.g. equidistantly spaced) and the gear teeth are located on a wobbling element capable of wobbling the gear teeth to plural offset (e.g. non-equidistantly spaced) positions. Such a wobbling offset arrangement also maximises the number of effective individual gear positions which are capable of being defined. An example of this aspect, is the wobbling wheel arrangement described herein.

In aspects, the clutch means is non-integral with either of the lid driving means or the indexing means, but forms a separate interconnecting component.

Suitably, the gearing surface comprises a gear wheel. As used herein, the term gear wheel encompasses, for example, a wheel, spindle or spool.

Suitably, the gear teeth may be arranged to be in ratchet form (i.e. enabling movement in one direction only).

Suitably, the gearing surface and gear teeth are in biased (e.g. sprung) engagement.

In one aspect, the lid driving means comprises a spiked wheel. As the spiked wheel turns, the lid sheet is pulled over it and the spikes perforate parts of the lid sheet to improve the grip on the lid sheet. The lid sheet then passes out into a chamber where it collects.

In another aspect, the lid driving means comprises a clamp system. The clamp system comprises at least one angled spring which is pivotable at one end and grips the lid sheet at the other end. The clamp system is moved in the direction that the lid sheet is to be pulled and grips the lid sheet, pulling it and therefore peeling it away from the base sheet. The clamp system is then moved back to its rest position. This results in the spring pivoting and clamping the lid sheet, therefore preventing the lid sheet from being further peeled from the base sheet.

In another aspect, the used portion of the lid sheet may be passed around rollers and fed back onto the used portion of the base sheet after the medicament has been accessed to join back onto the base sheet. The lid sheet may be coated with a sticky substance to aid resealing. The use of this mechanism saves space as the used portions of the blister strip will be collected in the same area.

In another aspect, the coil comprising the unused medicament carrier (e.g. blister strip) may be surrounded by a constant force spring. Alternatively, the coil comprising the unused blister strip may be surrounded by an elastomeric band or band comprising a contractible material. The constant force spring, elastomeric band or band comprising a contractible material contracts as the coil reduces in size.

Suitably, said peeling means additionally comprise a guide for guiding the lid sheet and base sheet along separate paths at the opening station. The lid sheet is passed around the guide portion onto the lid driving means.

Alternatively, the guide comprises a roller mechanism. The lid sheet is fed over the rollers onto the lid driving means.

Suitably, the internal mechanism additionally comprises a first chamber in which the strip is initially housed and from which it is dispensed and a second chamber to receive the used portion of the base sheet after it has been indexed around the index wheel and separated from the lid sheet.

Suitably, said first chamber and said second chamber are separated by a wall.

Suitably, said wall is movable to adjust the size of said first and second chambers.

In one aspect, the wall is pivotally mountable. Alternatively the wall is slidably mountable.

Suitably, the internal mechanism further comprises a third chamber to receive the used portion of the lid sheet and a fourth chamber which houses the index ratchet. The fourth chamber may communicate via a slit, which in turn extends upwardly within a mouthpiece and communicates with air inlets.

Suitably, the internal mechanism additionally comprises a crushing wheel to crush the medicament pockets after the medicament has been removed from them. The crushing wheel therefore reduces the space which the used portion of the base sheet takes up.

Typically, the internal mechanism for accessing said medicament contained within said medicament carrier is housed within a cassette.

Thus, in another embodiment, the invention provides a medicament dispenser for dispensing medicament comprising: a body; a holder, shaped to fit within said body and movable relative to said body; and receivable by said holder, said cassette containing the medicament carrier.

Suitably, the electronic drive system is located in either the body or the holder part, and the cassette comprises the minimum number of component (i.e. internal mechanism) parts. In embodiments, the body/holder including the electronic drive is designed to be retained by the user and the cassette is sold as a refill/reload component which is discarded after use. By locating the electronic drive system in the body/holder, the amount of electronic components which are discarded is minimised which is advantageous from an environmental standpoint.

Suitably, the cassette of the medicament dispenser herein comprises a) an opening station for receiving a pocket of the medicament carrier;
b) peeling means positioned to engage a base sheet and a lid sheet of a pocket which has been received in said opening station for peeling apart such a base sheet and lid sheet, to open such a pocket, said peeling means including lid driving means for pulling apart a lid sheet and a base sheet of a pocket that has been received at said opening station;
c) an outlet, positioned to be in communication with an opened pocket through which a user can remove medicament from such an opened pocket; and
d) indexing means for indexing in communication with said outlet, pockets of a medicament carrier in use with said medicament dispenser, wherein the lid driving means and/or said indexing means are operable by an electronic drive system located in the body or holder part.

Suitably, movement of the holder relative to the body results in movement of the cassette between a first position and a second position such that the cassette is reversibly removable from the holder when the cassette is in the second position.

Suitably the first position comprises a dispensing position. Preferably the second position comprises a non-dispensing position. The cassette is therefore only removable from the holder when the cassette is in the non-dispensing position.

Suitably, the holder and body include attaching means to attach the holder to the body. Preferably, said attaching means comprise a snap fit mechanism. Suitably said snap fit mechanism comprises a pin and hole system.

Suitably, the holder is pivotally movable relative to the body. Alternatively the holder is rotationally movable relative to the body.

Suitably the holder additionally comprises a stop to limit movement of the holder relative to the body. The stop abuts against the edge of the body at two points when it is rotated. At these points the holder may be designed to click into place. Therefore when the stop abuts one body edge then it is clicked into the dispensing position and when the stop abuts the other body edge then it is clicked into the non-dispensing position.

Alternatively the holder is slidably movable relative to the body.

Suitably, the holder additionally comprises a catch to retain the cassette. The catch may for example comprise a sprung pin which fits into a hole or an integral catch which deforms when pressed allowing removal of the cassette.

Suitably, the catch is child resistant. Child resistance may be realised by having a system which forces the user to perform two actions at once to remove the cassette. Other features of the catch may include shock or impact resistance, the ability to lock the catch and orientation features to ensure that the cassette can only be inserted one way. The catch should also be easy to manufacture and assemble, be robust, be composed of a minimal number of components and intrude minimally into the pace into which the cassette is inserted.

Suitably, the holder includes guide means to guide the cassette into the holder. Preferably said guide means comprise guide rails. Alternatively the guide means comprise grooves, indentations or other shaping or surface details to define a 'lock and key' relationship between the holder and the cassette. Colour guides, arrows and any other surface markings may also be employed.

Suitably, the cassette additionally comprises means to actuate the dispenser. The actuating means may take the form of a switch, push-button or lever.

Suitably, the cassette additionally comprises a mouthpiece.

Suitably, said mouthpiece is extendable. The mouthpiece extends as the cassette and holder are moved from the non-dispensing position to the dispensing position.

Alternatively the mouthpiece is retractable. The mouthpiece retracts as the cassette and holder are moved from the dispensing position to the non-dispensing position.

In one aspect, the mouthpiece is telescopic. In another aspect, the mouthpiece is fixed.

The medicament dispenser may also be designed for nasal inhalation of a powdered medicament and may therefore incorporate a nosepiece as an alternative to a mouthpiece. If the medicament is in solid form, the dispenser may incorporate an exit channel for tablet release.

Suitably, the body covers the mouthpiece and indexing lever when the cassette is in the non-dispensing position. This avoids the need for a separate cover and protects the mouthpiece from the ingress of dirt and contaminants during storage.

Suitably, the cassette additionally comprises a raised portion to fit against the holder. The raised portion is located at the opposite end of the cassette to the mouthpiece/nosepiece/exit and indexing lever and prevents the incorrect insertion of the cassette into the holder since it is too wide to fit into the holder. The raised portion is shaped such that it fits against a cut away part of the holder. Preferably said raised portion includes a section which is raised to define a grip portion.

Suitably, at least a portion of the holder and body are shaped for ease of grip by the user.

Suitably, operation of the dispenser may be performed with one hand.

Suitably, the medicament dispenser comprises an actuation or dose counter for counting the number of actuations of the indexing lever or releases of dose from the cassette.

The dose counter may count the number of doses left to be taken or the number of doses taken.

In one aspect, said dose counter is electronic. Alternatively said dose counter is mechanical.

In one aspect, said dose counter is located within the cassette. Alternatively, the dose counter is external to the cassette.

In one aspect, the blister strip has printed numbers on it corresponding to the doses in the pockets. Preferably, said printed numbers are visible through a window in the cassette.

The dispenser may be assembled as follows. The holder is snap fitted into the body. The cassette is assembled separately. The body of the cassette is formed, preferably in two sections with any necessary spindles or integral components formed into the base. Individual components such as indexing wheels, lid winding mechanisms, guide portions etc are then assembled into the base. Finally the medicament containing blister strip (or other suitable medicament carrier) may be inserted into the cassette. This may be wound into the dispenser before the lid is attached to the cassette and the cassette sealed. Alternatively, the cassette may be formed completely apart from a hole left in its side for insertion of the blister strip or medicament carrier. The hole may then be sealed to complete the cassette. This second method of inserting the medicament carrier into the dispenser has the advantage that it is much simpler.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system is arranged to be responsive to or activated by the voice of a user. Thus, for example the system may be switched on or off in response to a voice command.

The electronic data management system may be integral with the body. Alternatively, the electronic data management system forms part of a base unit which is reversibly associable with the body.

Suitably, the medicament dispenser additionally comprises a data input system for user input of data to the electronic data management system. Preferably, the data input system comprises a man machine interface (MMI) preferably selected from a keypad, voice recognition interface, graphical user interface (GUI) or biometrics interface.

Energy may be conserved by a variety of means to enable the device to operate for longer on a given source of energy, such as a battery. Energy conservation or saving methods have additional advantages in terms of reducing the size requirements of the power source (e.g. battery) and thus the weight and portability of the medicament dispenser.

A variety of energy saving methods is available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components.

Suitably, the system additionally comprises a visual display unit for display of data from the electronic data management system to the user. The display may for example, comprise a screen such as an LED or LCD screen. More preferably the visual display unit is associable with the body of the medicament dispenser.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement cassettes. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hard-wired link, an infrared link or any other suitable wireless communications link.

Suitably, the medicament dispenser additionally comprises an actuation detector for detecting actuation of the dispensing mechanism wherein said actuation detector transmits actuation data to the electronic data management system.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the release means. The time delay is typically of the order of from three to thirty seconds.

Suitably, the medicament dispenser additionally comprises a release detector for detecting release of medicament from the cassette, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector, or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the medicament dispenser additionally comprises a breath trigger for triggering the dispensing mechanism, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analysed waveform.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser comprises in association with a body or housing thereof, a first transceiver for transmitting and receiving data and in association with the medicament container, a second transceiver for transmitting and receiving data, wherein data is transferable in two-way fashion from the first transceiver to the second transceiver. The data is preferably in digital form and suitable for transfer by electronic or optical means. A medicament dispenser of this general type is described in pending UK Patent Application No. 0020538.5.

One advantage of embodiments of this type is the ability to store many types of information in different parts of the memory structure of the transceivers. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

On loading or reloading the medicament dispenser with a cassette the second transceiver may, for example, read the unique serial number, batch code and expiry date of the medicament and any other information on the second transceiver. In this way the nature and concentration of the medicament, together with the number of doses used or remaining within the cassette, may be determined. This information can be displayed to the patient on a visual display unit. Other information, such as the number of times the medicament dispenser has been reloaded with a cassette, may also be displayed.

Similarly, should the cassette be removed from the holder before the supply of medicament is exhausted, the same data can be read from the second transceiver and the number of doses remaining or used determined. Other information, such as the date and time of administration of the drug, or environmental exposure data such as the minimum/maximum temperatures or levels of humidity the cassette has been exposed to, may also be read and displayed to the user.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods outwith the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the device. Or alternatively, data may be stored in a database memory of the electronic data management system and periodically downloaded to any transceiver. In either case, a history of the usage of the device may be built up in the memory of a transceiver.

In one embodiment herein, a history of the usage of the medicament dispenser is transferred to the second transceiver. When the blister strip in the cassette is exhausted it is exchanged by the patient for a new refill cassette. At the point of exchange, which will typically occur at the pharmacy, data may be transferred from the exhausted cassette to the refill and vice-versa. Additionally, usage history data may be read from the refill and transferred to a healthcare data management system for example comprising a network computer system under the control of a healthcare data manager.

Methods are envisaged herein whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or one dispensing) to or from any transceiver can be arranged to be readily achievable by the use of a reader which is remote from the medicament dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly-powered and the term passive is used to mean indirectly-powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver. Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or holder of the medicament dispenser or on the cassette.

In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is mouldable or weldable to the cassette or housing. Suitably, the carrier encases the tag. More preferably, the carrier forms a hermetic seal for the tag.

In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 kHz to 2.5 GHz. Preferred operating frequencies are selected from 125 kHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system. Dispensers employing such communicators are described in pending PCT Applications No.s PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto. More preferably, information from the user-specific network address can be made available to the remote information source.

In one aspect, the remote information source is a medicament prescriber, for example a doctors practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests which have been remotely pre-authorised by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

Suitably, the medicament dispenser additionally comprises a geographic positioning system such as a global positioning system or a system which relies on the use of multiple communications signals and a triangulation algorithm.

Preferably the powdered medicament comprises a drug. Preferably the drug is selected from the group consisting of albuterol, saimeterol, fluticasone propionate and beclomethasone dipropionate and salts or solvates thereof and any combination thereof. Preferably said combination comprises salmeterol xinafoate and fluticasone propionate.

Preferably the powdered medicament additionally comprises an excipient. Preferably said excipient is a sugar.

According to another aspect of the present invention there is provided the medicament dispenser described above in kit of parts form. A first part of the kit comprises a body; a holder, shaped to fit within said body and movable relative to said body; and within said holder a receiving station for receipt of a cassette. A second part of the kit comprises a cassette containing a medicament carrier and internal mechanism for indexing said medicament carrier, wherein the cassette is receivable by the receiving station and movement of the holder relative to the body results in movement of the cassette between a first position and a second position such that the cassette is reversibly removable from the receiving station when the cassette is in the second position. The holder also comprises an electronic drive system for driving the internal indexing mechanism of the cassette.

In one aspect, the medicament dispenser may be assembled as follows. The holder is snap fitted into the body. The cassette is assembled separately. The body of the cassette is formed, preferably in two sections with any necessary spindles or integral components formed into the base. Individual components such as indexing wheels, lid winding mechanisms, guide portions etc are then assembled into the base. Finally the medicament carrier (e.g. an elongate blister pack) is inserted into the cassette. This may be wound into the dispenser before the lid is attached to the cassette and the cassette sealed. Alternatively, the cassette may be formed completely apart from a hole left in its side for insertion of the medicament carrier. The hole may then be sealed to complete the cassette. This second method of inserting the medicament carrier into the device has the advantage that it is much simpler.

BRIEF DESCRIPTION OF THE DRAWINGS

The invention will now be described with reference to the accompanying drawings in which:

FIGS. 4b and 4c show side views of the inner workings of the holder of the device of FIG. 4a;

FIGS. 4d and 4e show side views of the inner workings of the cassette of the device of FIG. 4a.

DETAILED DESCRIPTION OF THE DRAWINGS

Figure 1:
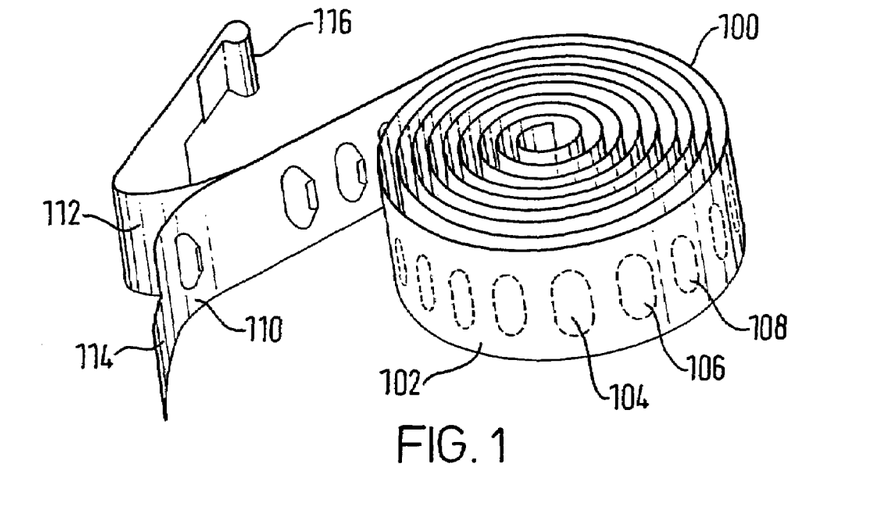
FIG. 1 shows a perspective view of a medicament carrier in accordance with the present invention.

Referring now to the Figures, FIG. 1 shows a medicament carrier 100 in accord with the present invention. The medicament carrier comprises a flexible strip 102 defining a plurality of pockets 104, 106, 108 each of which contains a dose of medicament which can be inhaled, in the form of powder.

The strip comprises a base sheet 110 in which blisters are formed to define the pockets 104, 106, 108 and a lid sheet 112 which is hermetically sealed to the base sheet except in the region of the blisters in such a manner that the lid sheet 112 and the base sheet 110 can be peeled apart. The sheets 110, 112 are sealed to one another over their whole width except for the leading end portions 114, 116 where they are preferably not sealed to one another at all. The lid 112 and base 110 sheets are each preferably formed of a plastics/aluminium laminate and are preferably adhered to one another by heat sealing.

The strip 102 is shown as having elongate pockets 104, 106, 108 which run transversely with respect to the length of the strip 102. This is convenient in that it enables a large number of pockets 104, 106, 108 to be provided in a given strip 102 length. The strip 102 may, for example, be provided with sixty or one hundred pockets but it will be understood that the strip 102 may have any suitable number of pockets.

Figure 2:
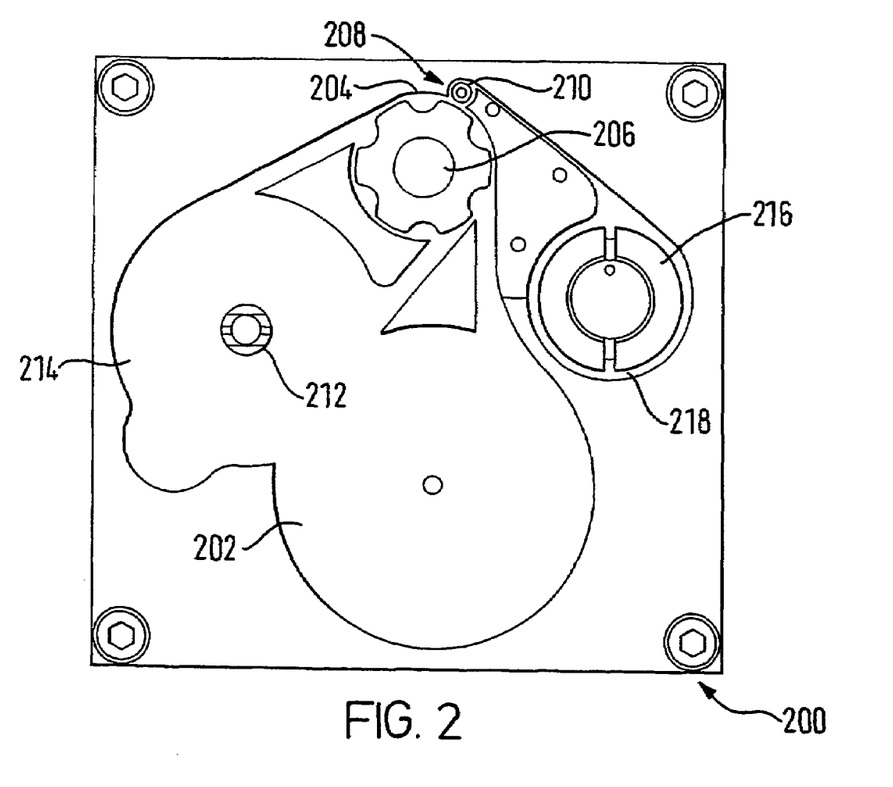
FIG. 2 shows a base unit housing an internal mechanism in accordance with one aspect of the invention.

FIG. 2 illustrates a base unit 200 of a medicament dispenser according to the invention. A medicament strip (not shown for clarity) is positioned in chamber 202 of the base unit 200. The strip is pre-fed through a guide member 204 within the manifold component and engaged in a six-pocket index wheel 206. The first pocket of the strip is positioned one pocket away from the opening station 208. The lid foil and base foil are separable about a beak 210. The resulting empty base foil is coiled about a base take-up spindle 212 in the base take-up chamber 214. The used lid foil is fed over the beak 210 and coiled about a lid take-up spindle 216 in the lid take-up chamber 218.

The dispenser is actuated by pressing a button on the side of the dispenser (not shown) which is linked to an electronic control system including a DC motor (not shown for clarity) to index the internal mechanism by one pocket of medicament. The DC motor thus indexes the strip and coils up the waste foils.

Initially, the gearing between the index wheel 206 and the lid take-up foil spindle 216 is one-to-one. However, as the lid take up spindle 216 winds on more foil, its effective winding diameter increases. An increase in diameter would cause the lid take-up spindle 216 to pull more strip than the index wheel 206 releases. Thus, in this particular example, the electronic control system is programmed to compensate for increase in lid spool diameter and adjust the amount the lid spool rotates accordingly.

Figure 3:
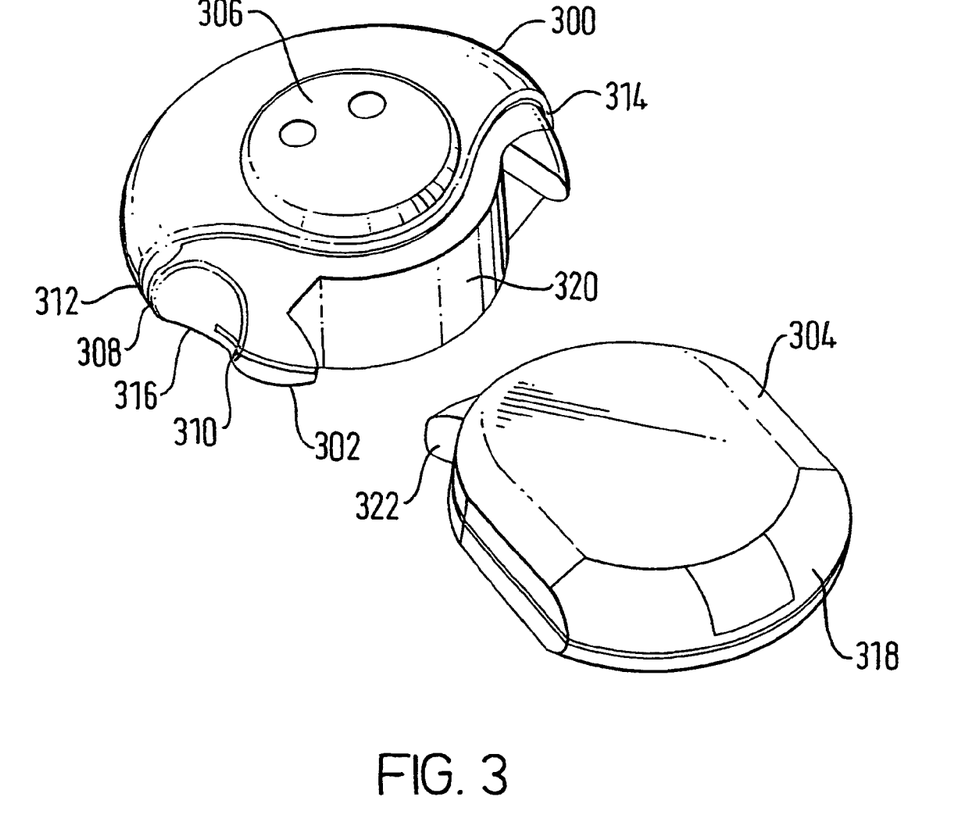
FIG. 3 shows a base unit housing an internal mechanism according to another aspect of the invention.

FIG. 3 shows a medicament dispenser in accord with the present invention, comprising a body 300, a holder 302, refill cassette 304 and electronic display 306. The holder 302 is shaped to fit snugly inside body 300 and is fixed to a point on the body (not shown) about which it rotates. Stops 308, 310 protrude from the holder 302 and prevent the holder 302 from rotating more than about 180° relative to the body 300. The stops 308, 310 also provide two defined positions of the holder 302 within the body 300. One position is defined by stop 308 meeting with body edge 312 and the other position defined by stop 310 meeting with body edge 314 when the holder has been rotated relative to the body. The area between stops 308 and 310 is shaped to form a thumb or finger grip 316 for the user of the device. The holder 302 forms a shell into which the refill cassette 304 snugly fits.

The refill cassette 304 comprises a shell containing the medicament carrier (not shown) and a mechanism for opening the carrier (not shown) for the medicament to be accessed. The refill cassette 304 has a raised portion 318 at one end on both sides along its width so that this part of the refill cassette 304 is at least the same depth as the part of the holder 320 which receives the refill cassette 304. This allows the position of the cassette 304 within the holder 302 to be fixed such that the ridge 318 protrudes from the holder 302 but the rest of the cassette 304 is contained within the holder 302.

The refill cassette 304 also has a mouthpiece (not shown) and an actuating push button 322 for actuating the DC motor for indexing the medicament carrier within the cassette 304.

FIGS. 4a to 4e illustrate a medicament dispenser according to another aspect of the present invention. The dispenser comprises a body 400 in the form of a cassette holder which receives a cassette 402. The cassette has a mouthpiece 404 which is covered by a rotating lid 406 when the cassette 402 is in situ in the body 400.

Figure 4A:
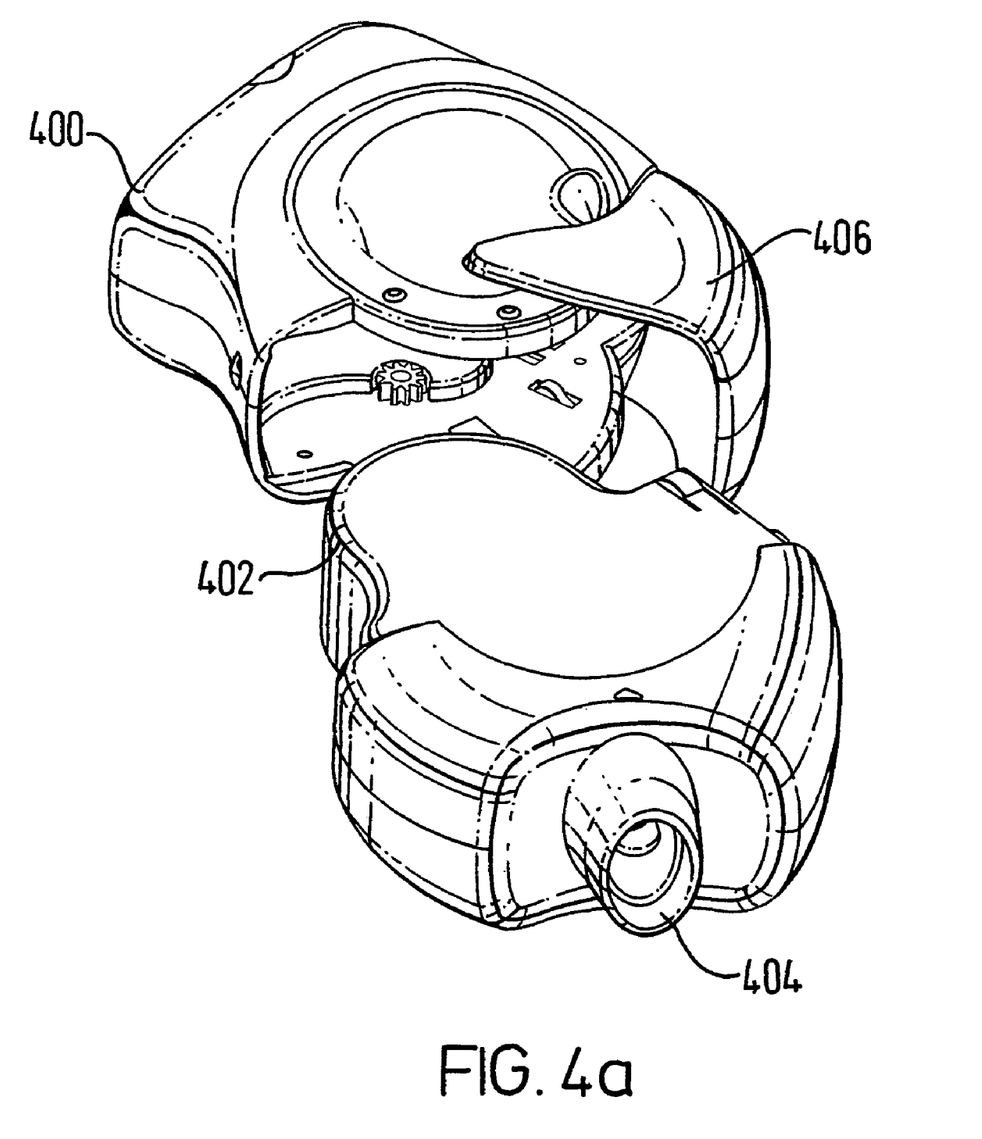
FIG. 4a shows a perspective view of a medicament dispenser, in the form of a holder/body and a refill cassette, according to the invention with the cassette removed from the holder/body.
Figure 4B:
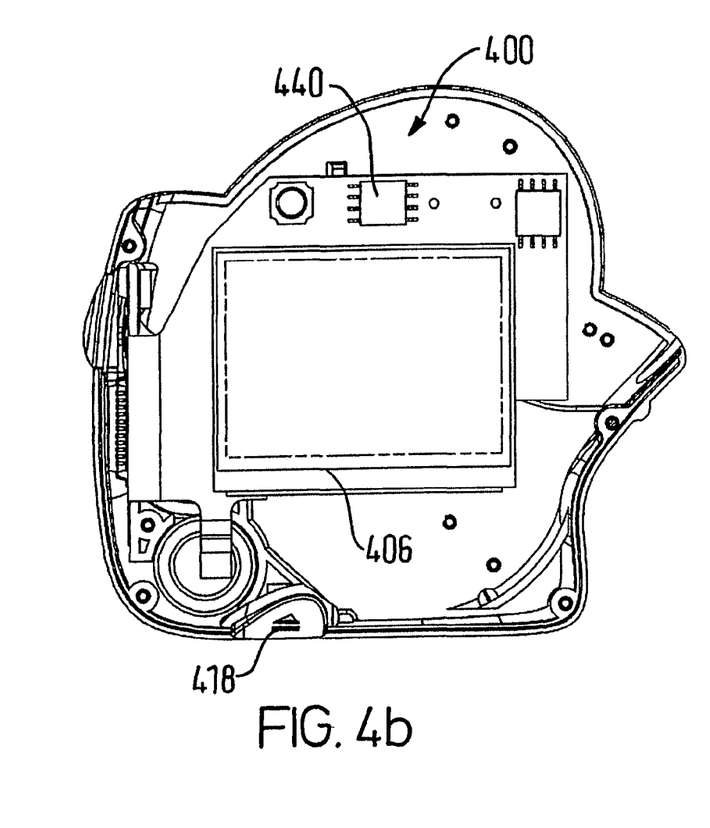
Figure 4C:
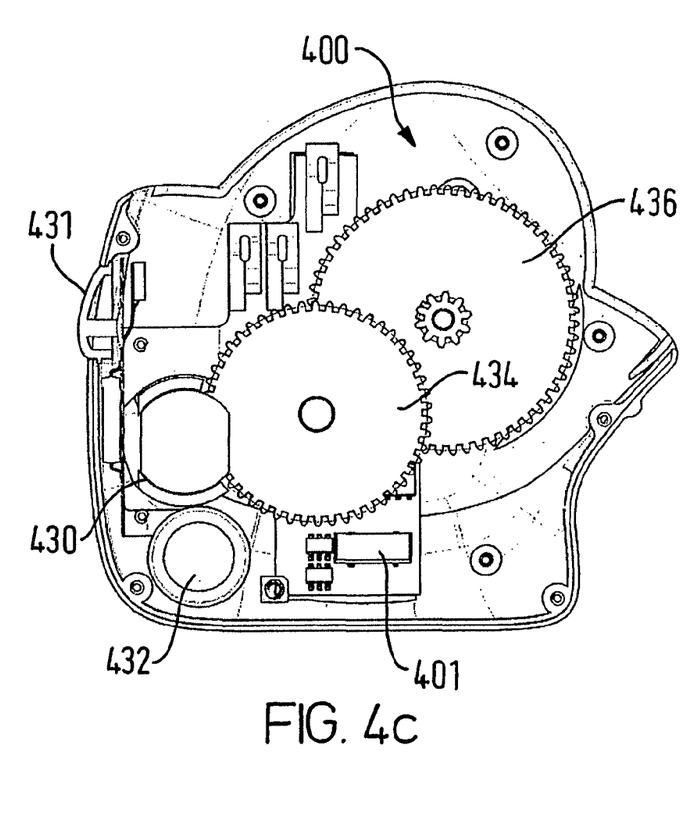

FIGS. 4b and 4c show a split-shell view of the holder 400 body shell. The body 400 is provided with DC motor 430 powered by battery 432, responsive to actuator switch 431. In use, the motor 430 drives gear wheels 434, 436, wherein gear wheel 436 drives foil spool 416 of the cassette 402 to advance a medicament dose. The body 400 is also provided with cassette release button 418 which releases a reversible catch mechanism (not shown) to enable mechanical release of a cassette 402 from the holder body 400. Electronic control system in the form of circuitry 440, 441 controls the DC motor 430, responsive to the actuator switch 431, and also controls LCD screen 406 for display of information to the user.

Figure 4D:
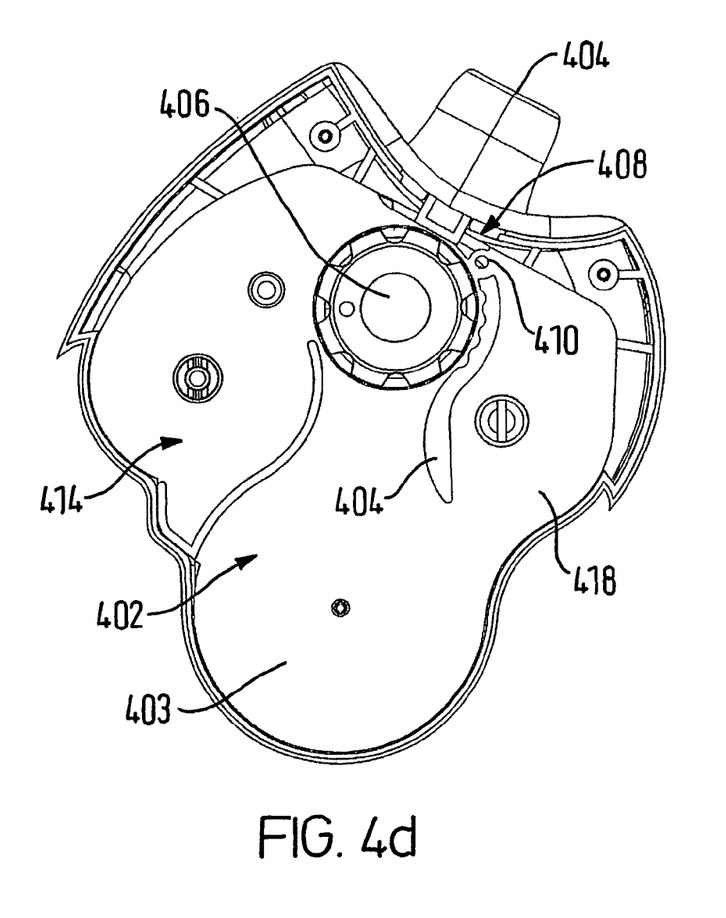
Figure 4E:
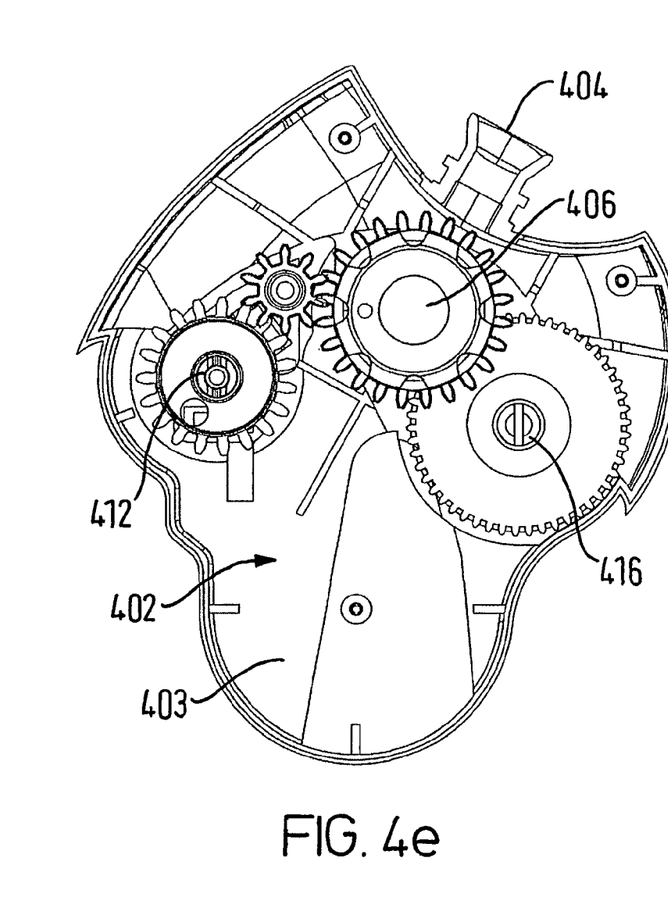

FIGS. 4d and 4e show the cassette 402 in more detail. A medicament strip (not shown for clarity) is positioned in chamber 403 of the cassette unit 402. The strip is pre-fed through a guide member 404 within the manifold component and engaged in a multi-pocket index wheel 406. The first pocket of the strip is positioned one pocket away from the opening station 408. The lid foil and base foil are separable about a beak 410. The resulting empty base foil is coiled about a base take-up spindle 412 in the base take-up chamber 414. The used lid foil is fed over the beak 410 and coiled about a lid take-up spindle 416 in the lid take-up chamber 418.

The dispenser of FIGS. 4a to 4e is actuated by pressing the actuator button 431 on the side of the dispenser which is linked to the electronic control system 440, 441 which controls DC motor 430 to index the internal mechanism by one pocket of medicament. The DC motor 430 thus indexes the strip and coils up the waste foils.

Initially, the gearing between the index wheel 406 and the lid take-up foil spindle 416 is one-to-one. However, as the lid take up spindle 416 winds on more foil, its effective winding diameter increases. An increase in diameter would cause the lid take-up spindle 416 to pull more strip than the index wheel 406 releases. Thus, in this particular example, the electronic control system 440, 441 is programmed to compensate for an increase in lid spool 416 diameter and adjust the amount the lid spool 416 rotates accordingly.

Figure 5:
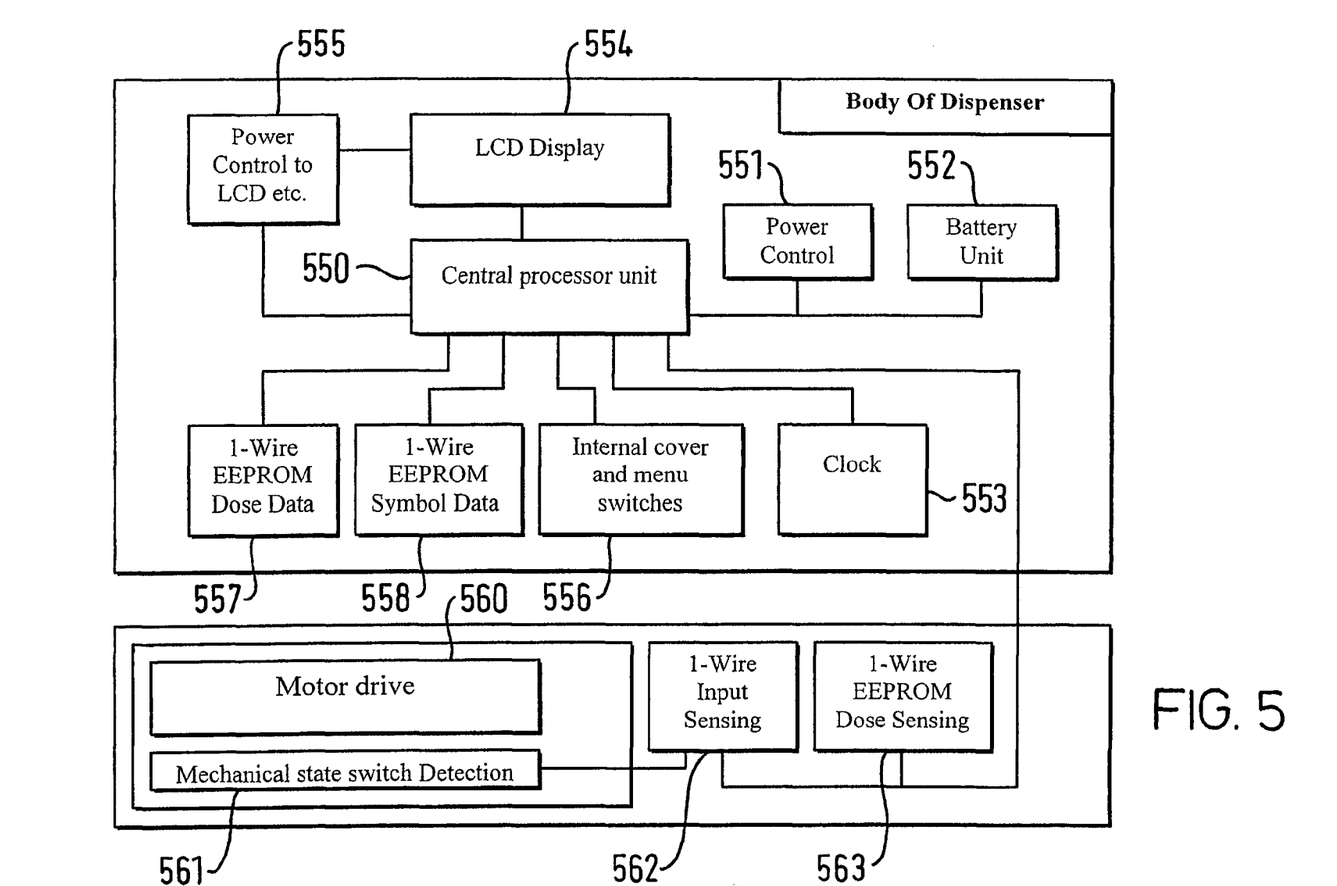
FIG. 5 shows a block diagram of an electronic drive system herein.

FIG. 5 shows a schematic view of an electronic control system suitable for use in a medicament dispenser herein. The control system is typically located in the body/holder of a refillable medicament dispenser (e.g. as shown in FIGS. 4a to 4e). Central processor unit (CPU) 550 communicates with power control 551; battery 552; and clock 553. The CPU 550 also communicates with various user input/output functions which in combination comprise a man machine interface (MMI). In more detail, the MMI comprises an LCD display 554; power control for the LCD 555; and menu/switch inputs 556. Various memories including EEPROM dose data memory 557 and EEPROM symbol data memory 558 also communicate with the CPU 550.

Importantly, the control system 550 also communicates with the motor drive 560 and switch detector 561 therefor. Sensors are provided to detect user input 562 (e.g. manual actuation of the dispenser) and release of dose 563 from the dispenser. In embodiments, the dispenser is provided with a power management system enabling various power saving modes such as 'sleep' and 'powered down' modes.

It may be appreciated that any of the parts of the dispenser or cassette which contact the medicament suspension may be coated with materials such as fluoropolymer materials (e.g. PTFE or FEP) which reduce the tendency of medicament to adhere thereto. Any movable parts may also have coatings applied thereto which enhance their desired movement characteristics. Frictional coatings may therefore be applied to enhance frictional contact and lubricants (e.g. silicone oil) used to reduce frictional contact as necessary.

The medicament dispenser of the invention is suitable for dispensing medicament, particularly for the treatment of respiratory disorders such as asthma and chronic obstructive pulmonary disease (COPD), bronchitis and chest infections. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R, 3R, 4S, 5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy) phenyl]-2-[((2S)-4-methyl-2-{[2-(2-methylphenoxy)acetyl] amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (eg as the fumarate salt) in combination with an anti-inflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

Generally, powdered medicament particles suitable for delivery to the bronchial or alveolar region of the lung have an aerodynamic diameter of less than 10 micrometers, preferably less than 6 micrometers. Other sized particles may be used if delivery to other portions of the respiratory tract is desired, such as the nasal cavity, mouth or throat. The medicament may be delivered as pure drug, but more appropriately, it is preferred that medicaments are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of the powdered medicament and/or excipient may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

The excipient may be included with the medicament via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:
1. A medicament dispenser for use with a medicament carrier having a plurality of pockets for containing medicament wherein said pockets are spaced along the length of and defined between two peelable sheets secured to each other, said dispenser having an internal mechanism for accessing said medicament contained within said medicament carrier, said mechanism comprising,
  a) an opening station for receiving a pocket of said medicament carrier;
  b) peeling means positioned to engage a base sheet and a lid sheet of a pocket which has been received in said opening station for peeling apart such a base sheet and lid sheet, to open such a pocket, said peeling means including lid driving means for pulling apart a lid sheet and a base sheet of a pocket that has been received at said opening station;
  c) an outlet, positioned to be in communication with an opened pocket through which a user can remove medicament from such an opened pocket; and
  d) indexing means for indexing in communication with said outlet, pockets of a medicament carrier in use with said medicament dispenser, wherein said lid driving means comprises a wheel on which the lid sheet is wound up, said lid sheet wheel has an effective winding surface the diameter of which increases after every use of the diameter as it winds on more lid sheet, and that said lid driving means are operated by an electronic drive system which comprises means to limit the extent of rotation of said wheel, in order to control the length of medicament carrier peeled by said peeling means so that the medicament carrier is indexed by the same amount on each use of the dispenser.

2. A medicament dispenser according to claim 1, wherein said electronic drive system is used in conjunction with a mechanical drive system.

3. A medicament dispenser according to claim 1, wherein said electronic drive system comprises a motor selected from the group consisting of a DC electric motor, a piezo-electric (PZ) motor, an ultrasonic motor, a solenoid motor a linear motor and any combinations thereof.

4. A medicament dispenser according to claim 1 further comprising actuating means for actuating said electronic drive system.

5. A medicament dispenser according to claim 4, wherein said actuating means is selected from the group consisting of a switch, a push-button, and a lever.

6. A medicament dispenser according to claim 1, wherein said indexing means comprise a rotatable index wheel having recesses therein, said index wheel being engageable with a medicament carrier in use with said medicament dispenser such that said recesses each receive a respective pocket of the base sheet of a medicament carrier in use with said medicament dispenser.

7. A medicament dispenser according to claim 1, wherein said wheel has a winding surface which decreases in diameter when tension in the lid sheet increases.

8. A medicament dispenser according to claim 1, wherein said lid driving means comprises at least one component selected from the group consisting of (i) a spool; (ii) a spiked wheel; and (iii) a spindle.

9. A medicament dispenser according to claim 1, wherein the internal mechanism additionally comprises a first chamber to receive the elongated strip of the medicament carrier when the base sheet and lid sheet are peelably sealed together and a second chamber to receive the base sheet after it has been separated from the lid sheet.

10. A medicament dispenser according to claim 1, wherein the internal mechanism for accessing the said medicament contained within said medicament carrier is housed within a cassette.

11. A medicament dispenser according to claim 10, wherein the body covers the mouthpiece and indexing lever when the cassette is in the non-dispensing position.

12. A medicament dispenser according to claim 10, wherein the cassette additionally comprises a raised portion to fit against the holder.

13. A medicament dispenser according to claim 10, wherein at least a portion of the body is shaped for ease of grip by the user.

14. A medicament dispenser according to claim 10, wherein the holder includes a thumb or finger grip.

15. A medicament dispenser according to claim 10, wherein operation of the device may be performed with one hand.

16. A medicament dispenser according to claim 10 comprising,
  a body;
  a holder, shaped to fit within said body and movable relative to said body; and
  receivable by said holder, said cassette containing said medicament carrier.

17. A medicament dispenser according to claim 16, wherein movement of said holder relative to said body results in movement of said cassette between a first position and a second position such that the cassette is reversibly removable from the holder when the cassette is in the second position.

18. A medicament dispenser according to claim 17, wherein the first position comprises a dispensing position.

19. A medicament dispenser according to claim 18, wherein the second position comprises a non-dispensing position.

20. A medicament dispenser according to claim 16, wherein the holder and body include attaching means to attach the holder to the body.

21. A medicament dispenser according to claim 20, wherein said attaching means comprise a pin and hole system.

22. A medicament dispenser according to claim 16, wherein the holder is slidably movable relative to the body.

23. A medicament dispenser according to claim 16, wherein the cassette additionally comprises a mouthpiece.

24. A medicament dispenser according to claim 23, wherein said mouthpiece is optionally extendable.

25. A medicament dispenser according to claim 23, wherein the mouthpiece is optionally retractable.

26. A medicament dispenser according to claim 23, wherein the mouthpiece is optionally telescopic.

27. A medicament dispenser according to claim 1 wherein the medicament is in powdered or solid form.

28. A medicament dispenser according to claim 27, wherein the meclicament comprises a drug.

29. A medicament dispenser according to claim 28, wherein the powdered medicament additionally comprises an excipient.

30. A medicament dispenser according to claim 29, wherein the excipient is a sugar.

* * * * *

UNITED STATES PATENT AND TRADEMARK OFFICE
CERTIFICATE OF CORRECTION

PATENT NO. : 7,231,920 B2  Page 1 of 1
APPLICATION NO. : 10/415319
DATED : June 19, 2007
INVENTOR(S) : Stephen James Harvey and Paul Kenneth Rand It is certified that error appears in the above-identified patent and that said Letters Patent is hereby corrected as shown below:

On the Title page:

Item (30)    Foreign Application Priority Data, please add

--Dec. 8, 2000   PCT/EP00/12389--

Column 24 at line 11:

please correct "meclicament" to read --medicament--

Signed and Sealed this

Fourth Day of December, 2007

JON W. DUDAS
*Director of the United States Patent and Trademark Office*